United States Patent [19]

Kearse

[11] 3,999,504
[45] Dec. 28, 1976

[54] INSULIN INJECTION REMINDER

[76] Inventor: George P. Kearse, 636 Pine St., Norco, La. 70079

[22] Filed: Sept. 22, 1975

[21] Appl. No.: 615,782

[52] U.S. Cl. .................... 116/121; 116/114 K; 116/136; 128/1 R

[51] Int. Cl.² .................. G09F 7/18; A61B 5/00

[58] Field of Search ...... 116/121, 136, 130, 114 K; 33/DIG. 1; 128/1 R

[56] References Cited

UNITED STATES PATENTS

| 1,656,993 | 1/1928 | Searle ................... 116/136 |
| 3,258,232 | 6/1966 | Nestecard ............... 116/114 K |
| 3,478,719 | 11/1969 | Sadoff, Jr. ............. 116/136 |
| 3,757,441 | 9/1973 | Baustin ................. 116/121 X |
| 3,841,260 | 10/1974 | Sharp et al. ............ 116/136 |

Primary Examiner—Donald O. Woodiel
Assistant Examiner—Daniel M. Yasich
Attorney, Agent, or Firm—Cantor and Singer

[57] ABSTRACT

An insulin injection reminder having a number of grids corresponding to the general injection areas of the body such as the arms, abdomen, thighs, and so forth. Each grid has a number of indicia corresponding to the specific injection sites within each general injection area.

9 Claims, 4 Drawing Figures

INSULIN INJECTION REMINDER

BACKGROUND OF THE INVENTION

This invention relates to the medical arts, and more specifically this invention relates to a device for maintaining a record of the rotation of insulin injections.

A large number of people are afflicted with diabetes in varying degrees of severity. Less severe cases can be treated by oral medication, but more severe cases are treated by injection of insulin. Since the insulin injections must be taken regularly on a strict schedule, the patient himself must administer the insulin. Also, close relatives of the diabetic patient are often trained to administer the insulin injections.

A complication of this self-administration system, however, exists in the fact that the site of injection must be changed systematically to insure good absorption of the medication and to prevent possible local dystrophies. Thus, the site of injection should be rotated regularly and there should be at least a thirty day interval before an injection is administered in the same place as a previous injection.

Furthermore, there are eight general areas where the insulin may be administered, these areas generally being in the upper arms, the abdomen, the thighs, and the hips. The injections are, therefore, rotated regularly among these areas and, in addition, rotated within these general areas.

Various means have been deviced for keeping track of where injections have been administered and where to administer succeeding injections. Usually, these means take the form of a home-made chart or table which can become cumbersome.

SUMMARY OF THE INVENTION

It is, therefore, a primary object of the present invention to provide a device for systematically keeping track of the sites of insulin injections and reminding the patient where to make the next succeeding injection which is simple and convenient to use.

It is another object of the present invention to provide an insulin injection reminder that is free of the disadvantages of the prior art devices.

It is still another object of the present invention to provide a method of determining the site for an insulin injection which is quick and simple to practice.

Pursuant to the foregoing objects, the device of the instant invention comprises a planar substrate containing a plurality of grids, each grid comprising a plurality of indicia, each grid corresponding to an injection area of the body and each of the indicia corresponding to a specific injection site within the area, and a means for denoting an injection site on the indicia.

This invention will be better understood and objects other than those set forth above will become apparent when consideration is given to the following detailed description thereof. Such description makes reference to the annexed drawing.

DESCRIPTION OF THE PREFERRED EMBODIMENTS

Figure 1A:
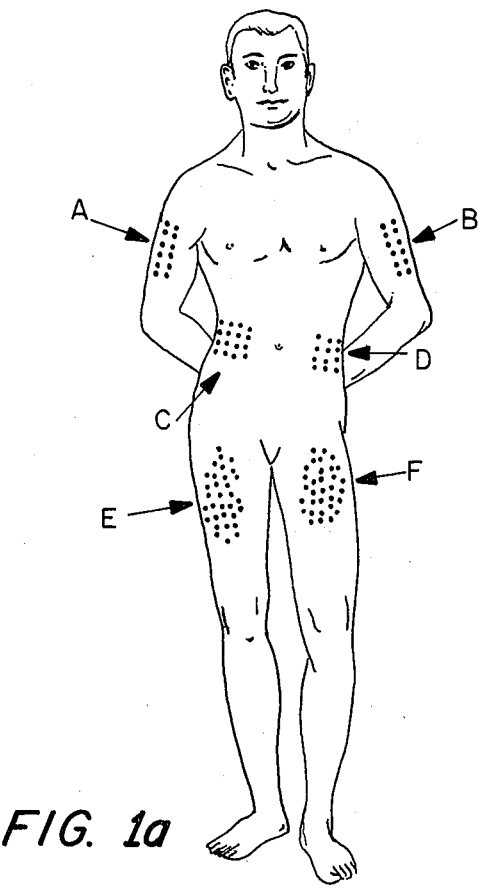
FIGS. 1a and 1b illustrate the injection areas of the body.
Figure 1B:
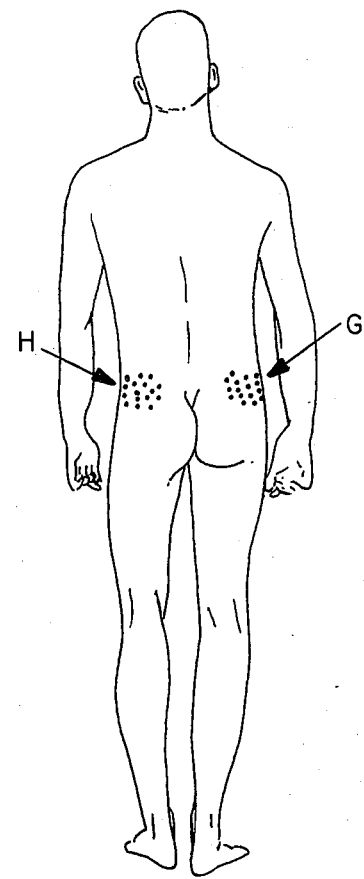

Referring first to FIGS. 1a and 1b, the general injection areas are shown on a sketch of a human body. The first of the areas where insulin injections are typically administered is in the upper arm. This area on the right arm is designated by the letter A and on the left arm by the letter B. The next area where the injections are typically administered is in the abdomen or stomach area and the right abdomen is designated by the letter C while the left abdomen is designated by the letter D. The third injection area is on the thighs or upper legs and the injection area on the right thigh is designated by the letter E while that on the left thigh is designated by the letter F. Finally, a fourth area used for insulin injection is on the hip. The injection area on the right hip is designated by the letter G while that on the left hip is designated by the letter H.

Figure 2:
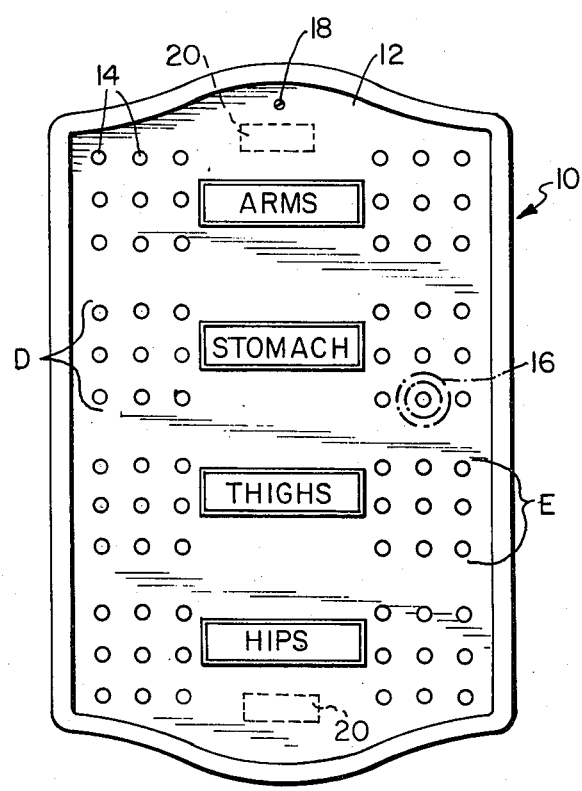
FIG. 2 is a plan view of a preferred embodiment of the device of the instant invention.

Turning to FIG. 2, the device of the instant invention is generally designated by the numeral 10. The device 10 comprises a flat or planar substrate 12 having a plurality of grids generally corresponding to each of the injection areas indicated in FIGS. 1a and 1b. For ease of illustration, only two of the grids on FIG. 2 are labelled in a manner corresponding to that of FIGS. 1a and 1b. Grids on the left and right sides of the substrate also correspond to injection areas on the left and right sides of the body. Each of the grids comprises a plurality of indicia 14, each of the indicia 14 denoting a specific injection site. As shown in FIG. 2, the grids corresponding to the injection areas can be labelled generally as "arms," "stomach" (or "abdomen"), and so forth. This, of course, is for the convenience of the user. Additionally, it will be clear to one of ordinary skill in the art that the precise shape of the planar substrate 12 is not material. It can be square or rectangular, it can be in the form of a human body, or it can be any other ornamental shape.

Figure 3:
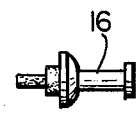
FIG. 3 is an elevational view of means for denoting the injection site on the device of the preferred embodiment.

In the preferred embodiment, shown in FIG. 2, the substrate 12 is fabricated of wood although it can be fabricated of any other rigid material such as a composition board or even metal or plastic. The indicia 14 in this preferred embodiment are holes which can be bored in the case of wood or metal or molded in the case of plastic. Means for denoting an injection site 16 is shown in FIG. 3 as a peg which fits in one of the holes 14.

As an alternative construction, the substrate 12 could be made of a rigid porous material such as cork or a similar composition and the means for denoting an injection site could be printed or painted on in a manner well-known in the art.

In either of the preceding embodiments, means are provided for mounting the device 10 on some other surface for convenience of reference. Such means could take the form of a screw or nail 18 attaching the device to a wall or at least one magnet 20 on the back of the device which would aid in attaching the device to a magnetically attractive metal surface. Most conveniently, since the insulin is normally stored in a refrigerator, the device can be mounted on the refrigerator door or metallic medicine cabinet wall, by means of magnets. Thus, the device would be readily available for reference.

The size of the device can also vary within wide limits and can be fairly large, in the order of 6 to 10 inches long, when used as a wall or a refrigerator mounted device, or could be small, in the order of 2 to 5 inches, when used as a portable device, perhaps attached to a typical hypodermic syringe carrying case.

In another embodiment, the device has printed indicia on paper with a plurality of such printed injection reminders bound together in a pad. In this embodiment, indicia corresponding to injection sites already used can be crossed off with a writing instrument.

Since the basic objects underlying the use of the insulin injection reminder device of the instant invention include the regular rotation of specific injection sites and maintaining a record of those sites used and those yet to be used, the actual method of use can vary according to personal preference. For instance, if the patient followed an unvarying routine of moving from one injection area to another and injecting himself in the same relative injection site of each area in order, a single injection site denoting means can be used. For instance, taking a patient who first injects himself in a site corresponding to the upper left hole of the left arm grid, then moving to the upper left hole of the right arm grid, followed by the upper left hole of the left abdomen grid and so forth, he can insert the denoting means 16 into the upper left hole of the left arm grid after administering the first injection, then moving the denoting means to the upper left hole of the right arm grid after administering the second injection, and so forth. After completing the first cycle of injections in the site corresponding to the upper left hole of each grid, he would then return to the left arm and administer an injection corresponding to the upper middle hole of the left arm grid, and so forth. Assuming the patient administers injections in all eight general areas shown in FIGS. 1a and 1b, and does this once each day, 72 days will have passed before returning to the initial injection site.

Other patients who do not follow as systematic a pattern, can insert a denoting means 16 into the hole corresponding to each site used and will then know that injection sites corresponding to blank holes are yet to be used. Furthermore, if a patient desires not to administer as many as nine injections in each general injection area, he can skip certain of the specific injection sites such as those denoted by the corner indicia in each grid. He will then be using five injection sites in each area.

Certain preferred embodiments have been described wherein pegs fit into holes in the substrate, stick-pins fit into a cork or other porous material substrate, and printed indicia are marked with a writing instrument. Another preferred embodiment contemplates either the substrate or the denoting means being made of a magnetically attractive material and the denoting means or the substrate, respectively, being magnetic, that is, a material which is magnetized. Thus, the substrate can be a magnetic metal and a plurality of denoting means would be magnets. Or, the substrate could be magnetized and the denoting means a magnetic metal. Another alternative would be for the substrate to be wood, cork, or the like, and the indicia to be embedded, or backed by, magnetic material or magnets. By "magnetically attractive material" and "magnetic material" is meant any material having the property of being attracted by a magnet, such as ferrous metals.

It should be apparent from the foregoing detailed description that the objects set forth hereinabove have been successfully achieved. Moreover, while there is shown and described present preferred embodiments of the invention it is to be distinctly understood that the invention is not limited thereto but may be otherwise variously embodied and practiced within the scope of the following claims. Accordingly,

What is claimed is:

1. As an article of manufacture, a device for maintaining a record of the previously used sites of, and selecting the next succeeding site for, insulin injections comprising a mountable planar substrate containing a plurality of spaced grids, each grid comprising a plurality of indicia means, the total number of said indicia means on said substrate being at least thirty, each said grid corresponding to a separate general injection area of the human body, and each of said indicia means within a given grid corresponding to a separate specific insulin injection site within said general body area represented by said given grid, and a denoting means selectively coactable with each of said indicia means for denoting each of said indicia means corresponding to injection sites which have been previously used, whereby each succeeding injection site is selected so as to maintain a regular schedule of rotation both among said general body areas and among said specific injection sites within each said general body area represented by the grids in order to provide an interval of at least thirty days between successive uses of the same specific injection site.

2. A device as claimed in claim 1, wherein said substrate is fabricated of a hard, rigid material, said indicia means are holes, and said denoting means are pegs adapted to fit into said holes.

3. A device as claimed in claim 1, wherein said substrate is fabricated of a rigid, porous material, said indicia means are imprinted thereon, and said denoting means include stick-pin members for inserting into said substrate at said indicia.

4. A device as claimed in claim 1, further comprising means for mounting said device on the surface of another object.

5. A device as claimed in claim 4, wherein said mounting means comprises at least one magnet on the reverse side of said substrate.

6. a device as claimed in claim 1, wherein said substrate is paper.

7. A device as claimed in claim 1, wherein one of said substrate and said denoting means comprises a magnetically attractive material and the other of said substrate and said denoting means comprises magnet means.

8. A device as claimed in claim 1, wherein each said grid corresponds to a separate general injection area of the human body selected from the group consisting of right and left arms, right and left abdomen, right and left thighs, and right and left hips.

9. A device as claimed in claim 1, wherein the total number of said grids on said substrate is eight, and each grid comprises at least five of said indicia means.

* * * * *